US012564711B2

(12) United States Patent
Wang et al.

(10) Patent No.: US 12,564,711 B2
(45) Date of Patent: Mar. 3, 2026

(54) METHOD AND DEVICE FOR MANAGING PROCESSING ACTIVITY PATTERNS

(71) Applicant: Pacesetter, Inc., Sylmar, CA (US)

(72) Inventors: Hanbiao Wang, Woodland Hills, CA (US); Xing Pei, Thousand Oaks, CA (US)

(73) Assignee: Pacesetter, Inc., Sylmar (CA)

( * ) Notice: Subject to any disclaimer, the term of this patent is extended or adjusted under 35 U.S.C. 154(b) by 886 days.

(21) Appl. No.: 16/853,918

(22) Filed: Apr. 21, 2020

(65) Prior Publication Data

US 2021/0327574 A1 Oct. 21, 2021

(51) Int. Cl.
*A61N 1/00* (2006.01)
*A61N 1/02* (2006.01)

(52) U.S. Cl.
CPC .................................... *A61N 1/025* (2013.01)

(58) Field of Classification Search
None
See application file for complete search history.

(56) References Cited

U.S. PATENT DOCUMENTS

| | | | | |
|---|---|---|---|---|
| 5,792,201 A | * | 8/1998 | Causey, III | .......... A61N 1/3931 607/27 |
| 6,128,528 A | | 10/2000 | Ericksen et al. | |
| 6,687,543 B1 | | 2/2004 | Isaac et al. | |
| 8,555,281 B1 | * | 10/2013 | van Dijk | ............... G06F 9/4881 718/100 |

| | | | | |
|---|---|---|---|---|
| 2008/0140141 A1 | * | 6/2008 | Ben-David | ........ A61N 1/36114 607/9 |
| 2015/0082076 A1 | * | 3/2015 | Jagmag | ..................... G06F 1/04 713/600 |
| 2015/0151131 A1 | | 6/2015 | Huelskamp et al. | |
| 2019/0364111 A1 | * | 11/2019 | Sloan | .................... H04W 12/08 |

FOREIGN PATENT DOCUMENTS

| | | |
|---|---|---|
| EP | 0750921 A2 | 1/1997 |

OTHER PUBLICATIONS

Extended European Search Report and Written Opinion for corresponding EP Application No. 21153921.5-1122 dated Jun. 29, 2021 (8 pages).

* cited by examiner

*Primary Examiner* — William J Levicky
*Assistant Examiner* — Anant A Gupta
(74) *Attorney, Agent, or Firm* — Dean D. Small; Carroll, Hoette & Butscher, LLC

(57) ABSTRACT

Methods, devices and program products are provided and include memory to store a baseline task handling (TH) pattern and TH circuitry including one or more processors. The TH circuitry is configured to perform tasks associated with one or more of collecting one or more CA signals or environmental event signals. The TH circuitry analyzes the one or more CA signals or environmental event signals, delivers therapy, detects communications requests, or maintains communications sessions with an external device. The IMD monitors a TH characteristic in connection with the performing the tasks, compares the TH characteristic to the baseline TH pattern and implements a corrective action in response to the compare of the TH characteristic and the baseline TH pattern.

20 Claims, 5 Drawing Sheets

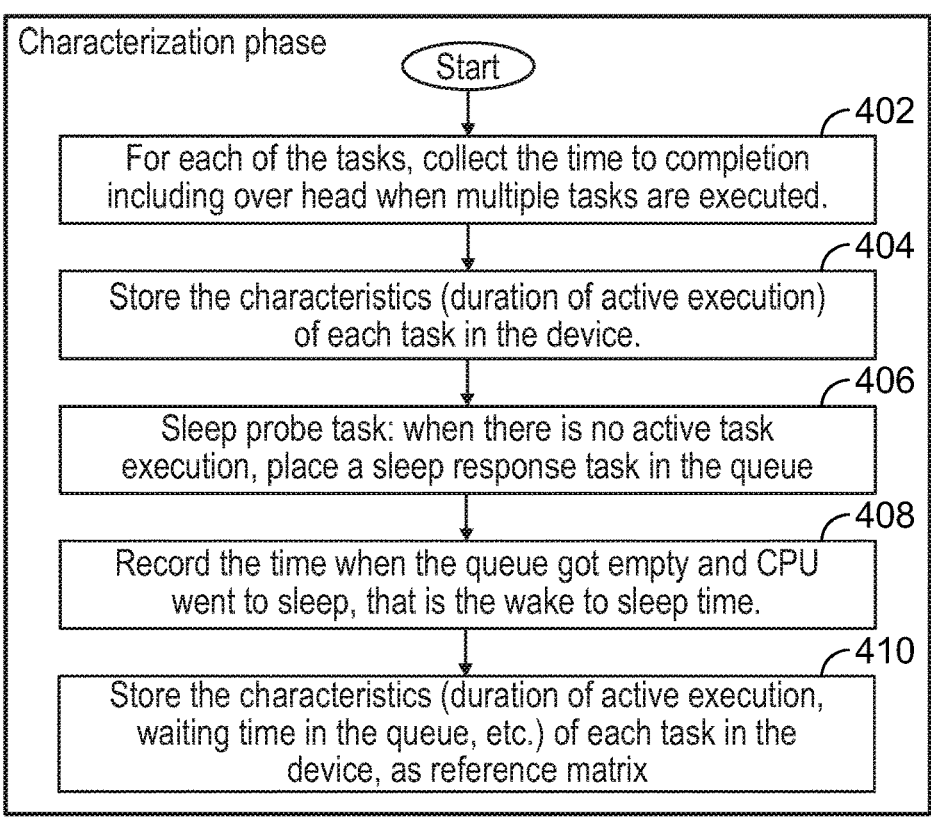

Characterization phase

Start

402
For each of the tasks, collect the time to completion including over head when multiple tasks are executed.

404
Store the characteristics (duration of active execution) of each task in the device.

406
Sleep probe task: when there is no active task execution, place a sleep response task in the queue

408
Record the time when the queue got empty and CPU went to sleep, that is the wake to sleep time.

410
Store the characteristics (duration of active execution, waiting time in the queue, etc.) of each task in the device, as reference matrix

FIG. 4

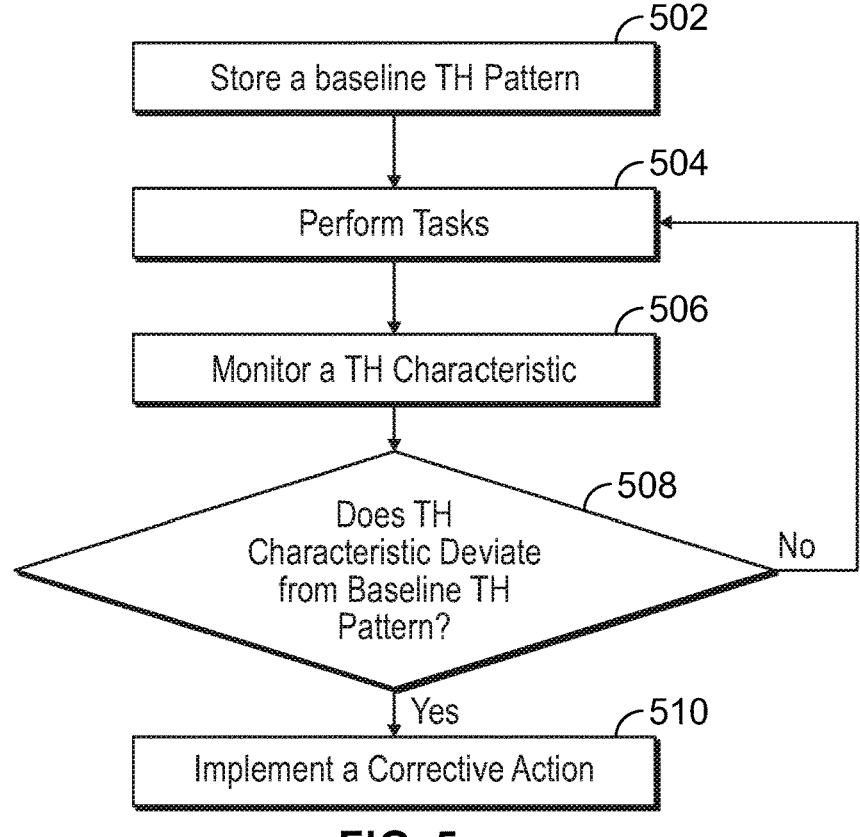

502
Store a baseline TH Pattern

504
Perform Tasks

506
Monitor a TH Characteristic

508
Does TH Characteristic Deviate from Baseline TH Pattern?

No

Yes

510
Implement a Corrective Action

METHOD AND DEVICE FOR MANAGING PROCESSING ACTIVITY PATTERNS

BACKGROUND

Embodiments of the present disclosure generally relate to methods and devices for managing a processing activity pattern of an implantable medical device.

Modern implantable medical devices (IMDs) (e.g., Implantable Cardioverter Defibrillators (ICDs)) are sophisticated battery-powered sub-systems with many components. IMDs must complete many complex tasks that may arise at any time. Such tasks commonly need to be completed with limited latency. Examples of tasks that need to be completed with limited latency include performing sensing, performing pacing, recording and analyzing rhythms, diagnosing episodes and providing lifesaving therapy based on diagnosis, performing self-check operations, handling long-range and short-range communication, and the like. Accordingly, IMDs require a central processing unit (CPU) capable of handling these tasks. To optimize task handling for real-time performance, typically IMD tasks are interrupt based. For example, the more time-critical tasks are handled in the interrupt context, while the less time-critical tasks are queued as events to be executed outside of the interrupt context, when there is no more pending interrupts to handle. Task handling inside and outside the interrupt context are conventionally referred to as foreground and background processing, respectively.

The CPU of the IMD consumes energy based on the amount of foreground and background processing tasks that need to be performed, thereby impacting the longevity of the battery of the IMD. It is preferred that the battery last for several years. To conserve energy, a CPU will enter a "sleep mode" after completing queued tasks. The ratio of the CPU running time (e.g., the time to complete all queued tasks) over the total time (e.g., CPU running time+CPU sleep time) represents the duty cycle of the CPU. In IMD design, it is desirable to keep the average duty cycle of the CPU as low as possible (e.g., 10% or less). Unexpected and/or undesirable duty cycle increases and/or task handling times consume additional energy, leading to premature battery depletion.

Additionally, IMDs employ detection functions that are dedicated to known failure modes experienced by firmware, hardware, and cyber security. However, an opportunity always exists for the IMD to experience unexpected or new failure modes that would otherwise be missed by the conventional failure mode detection controls. During unexpected or new failure modes, the CPU is vulnerable to operating at an abnormally high duty cycle and/or with an increased task handling time due to unexpected code deficiencies, hardware component failures, cyber security attacks, or the like.

A need remains for methods and devices that detect and manage undesirable increases in duty cycles and task handling characteristics of IMDs to mitigate potential malfunctions and/or failures in firmware, hardware, or cybersecurity and/or premature battery depletion.

SUMMARY

In accordance with embodiments herein, an implantable medical device (IMD) is provided. The IMD includes memory to store a baseline task handling (TH) pattern and TH circuitry including one or more processors. The TH circuitry is configured to perform tasks associated with one or more of collecting one or more CA signals or environmental event signals. The TH circuitry analyzes the one or more CA signals or environmental event signals, delivers therapy, detects communications requests, or maintains communications sessions with an external device. The IMD monitors a TH characteristic in connection with the performing the tasks, compares the TH characteristic to the baseline TH pattern and implements a corrective action in response to the compare of the TH characteristic and the baseline TH pattern.

Optionally, the corrective action may be implemented in response to the compare indicating that the TH characteristic has deviated from the baseline TH pattern by more than a predetermined margin. The TH characteristic may represent at least one of a CPU TH time characteristic, a CPU continuous active duration, a CPU continuous sleep duration, a duty cycle measurement for a select period of time, a queue waiting time for a task, an execution time for a critical task, a queue waiting time for a group of tasks, or an execution time for a group of tasks.

Optionally, the TH characteristic may represent the CPU TH time characteristic for at least one of i) time to complete a type of sense event analysis; ii) time to complete a type of external input processing; iii) a time to prepare and deliver a therapy; iv) a time to perform a measurement; v) a time to collect and update a diagnostic based on the CA signals; vi) a time to complete a housekeeping task; vii) a time to analyze an incoming data packet; and viii) a time to transmit an outgoing data packet.

Optionally, the monitor operation may include identifying, as part of the TH characteristic, a duty cycle of a CPU and the compare operation may include determining whether the duty cycle the CPU indicates that the CPU is continuously active for at least a predetermined amount of time. The duty cycle of the CPU may be determined as an average duty cycle over a first period of time periodically over a longer second period of time.

Optionally, the monitor operation may include maintaining at least one of a histogram of a wait time in which a task remains in a queue or a histogram of an execution time for select critical tasks. The implement operation may include at least one of providing an alert, terminating a task or process that is in progress, restart a task or process, or re-boot a portion or all of the processes implemented by the IMD.

In another embodiment, a method of managing a processing activity pattern of an implantable medical device (IMD) is provided. The method stores a baseline task handling (TH) pattern and performs tasks associated with one or more of collecting one or more CA signals or environmental event signals. The method analyzes the one or more CA signals or environmental event signals, delivers therapy, detects communications requests and maintains communications sessions with an external device. The method monitors a TH characteristic in connection with the performing the tasks, compares the TH characteristic to the baseline TH pattern and implements a corrective action in response to the compare of the TH characteristic and the baseline TH pattern.

Optionally, the corrective action may be implemented in response to the compare indicating that the TH characteristic has deviated from the baseline TH pattern by more than a predetermined margin. The TH characteristic may represent at least one of a CPU TH time characteristic, a CPU continuous active duration, a CPU continuous sleep duration, a duty cycle measurement for a select period of time, a queue waiting time for a task, an execution time for a critical task, a queue waiting time for a group of tasks, or an execution time for a group of tasks.

Optionally, the TH characteristic may represent the CPU TH time characteristic for at least one of: i) time to complete a type of sense event analysis; ii) time to complete a type of external input processing; iii) a time to prepare and deliver a therapy; iv) a time to perform a measurement; v) a time to collect and update a diagnostic based on the CA signals; vi) a time to complete a housekeeping task; vii) a time to analyze an incoming data packet; and viii) a time to transmit an outgoing data packet.

Optionally, the method may monitor operation includes identifying, as part of the TH characteristic, a duty cycle of a CPU and the compare operation may include determining whether the duty cycle the CPU indicates that the CPU is continuously active for at least a predetermined amount of time. The duty cycle of the CPU may be determined as an average duty cycle over a first period of time periodically over a longer second period of time.

Optionally, the monitor operation may include maintaining at least one of a histogram of a wait time in which a task remains in a queue or a histogram of an execution time for select critical tasks. The implement operation may include at least one of providing an alert, terminating a task or process that is in progress, restart a task or process, or re-boot a portion or all of the processes implemented by the IMD.

In accordance with embodiments herein, a computer program product is provided. The computer program product includes a non-transitory computer readable storage medium comprising computer executable code to perform tasks associated with one or more of collecting the CA signals, analyzing CA signals, delivering therapy, detecting communications requests, maintaining communications sessions with an external device. The computer program product monitors a TH characteristic in connection with the performing the tasks, compares the TH characteristic to the baseline TH pattern and implements a corrective action in response to the compare of the TH characteristic and the baseline TH pattern.

Optionally, the corrective action may be implemented in response to the compare indicating that the TH characteristic has deviated from the baseline TH pattern by more than a predetermined margin. The TH characteristic may represent at least one of a CPU task handling time characteristic, a CPU continuous active duration, a CPU continuous sleep duration, a duty cycle measurement for a select period of time, a queue waiting time for a task, an execution time for a critical task, a queue waiting time for a group of tasks, or an execution time for a group of tasks.

Optionally, the TH characteristic may represent the CPU TH time characteristic for at least one of: i) time to complete a type of sense event analysis; ii) time to complete a type of external input processing; iii) a time to prepare and deliver a therapy; iv) a time to perform a measurement; v) a time to collect and update a diagnostic based on the CA signals; vi) a time to complete a housekeeping task; vii) a time to analyze an incoming data packet; and viii) a time to transmit an outgoing data packet.

BRIEF DESCRIPTION OF THE DRAWINGS

FIG. 4 illustrates a characterization process for determining and storing TH characteristics in accordance with embodiments herein.

FIG. 5 illustrates a process for managing a processing activation pattern of an IMD in accordance with embodiments herein.

DETAILED DESCRIPTION

Figure 1:
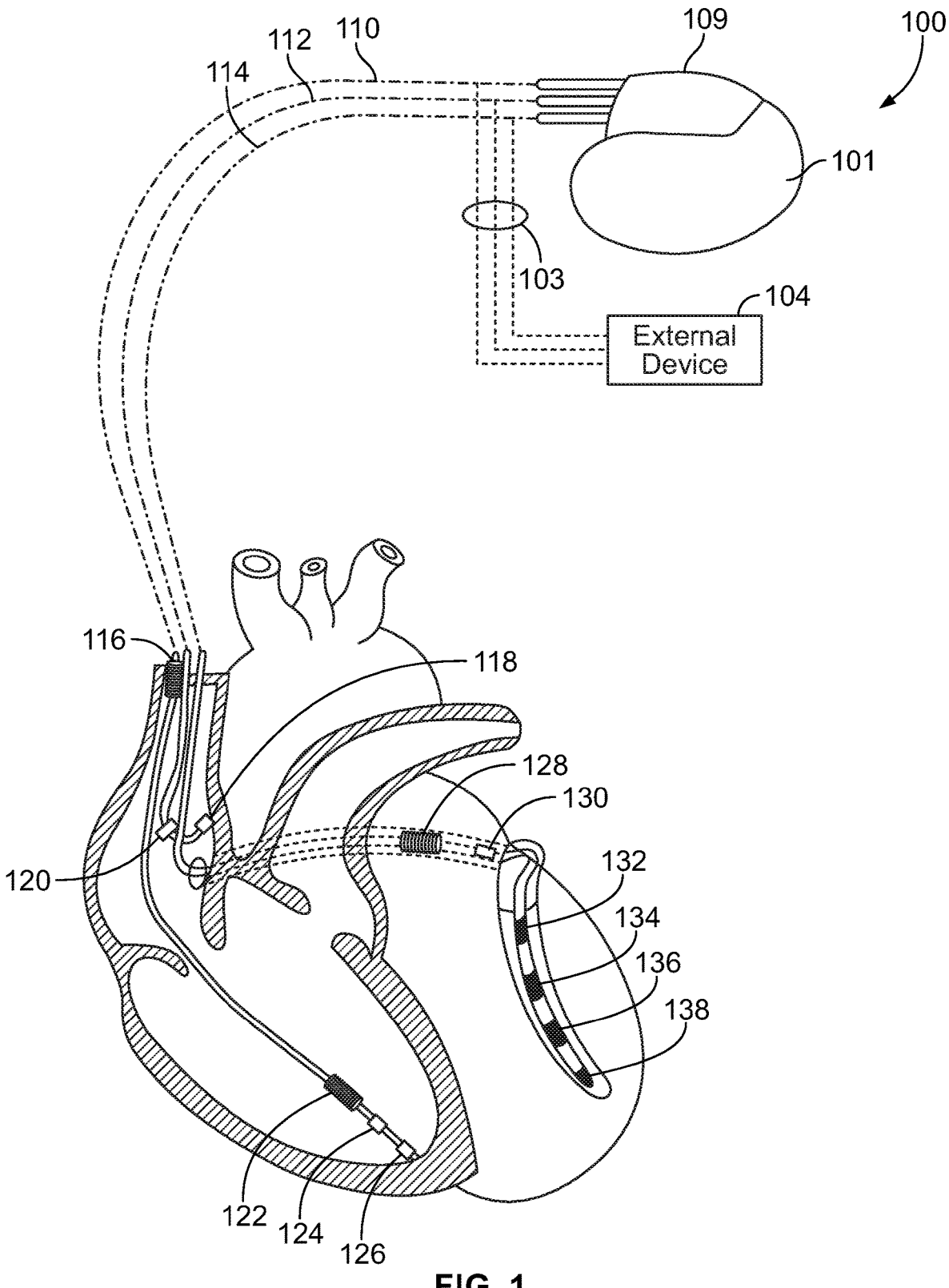
FIG. 1 illustrates an IMD and external device coupled to a heart in a patient and implemented in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "task" shall mean a predefined operation to be performed by a medical device over a useful life of the medical device. The predefined operations may be in connection with delivering therapy, monitoring signals, analyzing signals, communicating with other devices, self-diagnostics, internal maintenance, and the like. Nonlimiting examples of tasks include reforming capacitors, delivering shocks or other therapy, performing telemetry operations, transmitting and receiving RF communications, performing expected self-discharge (about 1% per year) and the like.

The terms "task handling characteristic" and "TH characteristic" shall mean an attribute of a medical device measurable in connection with performing one or more tasks. Non-limiting examples of TH characteristics include a CPU TH time characteristic, a CPU continuous active duration (e.g., a duration of time where the CPU is continuously active and performing tasks in a queue), a CPU continuous sleep duration (e.g., a duration of time where the CPU is continuously inactive/in a sleep mode and does not perform any tasks), a duty cycle measurement for a select period of time, a queue waiting time for a task, an execution time for a critical task, a queue waiting time for a group of tasks, an execution time for a group of tasks, or the like. Additionally or alternatively, the TH time characteristic may include one or more of i) time to complete a type of sense event analysis; ii) time to complete a type of external input processing; iii) a time to prepare and deliver a therapy (e.g., a V pulse); iv) a time to perform a measurement (e.g., an impedance measurement, a battery charge measurement, etc.); v) a time to collect and update a diagnostic based on the cardiac activity (CA) signals; vi) a time to complete a housekeeping task; viii) a time to analyze an incoming data packet; ix) a time to transmit an outgoing data packet; and the like.

The terms "processing activity pattern", "task handling pattern" and "TH pattern" shall mean a pattern of one or more TH characteristics associated with one or more completed tasks over a period of time. A TH pattern may include trends in one or more TH characteristics measured over a period of time. For example, a TH pattern may include a histogram of one or more TH characteristics associated with one or more tasks (e.g., a histogram of the wait time and/or the execution time associated with a task).

The term "duty cycle" shall mean an amount/percentage of time over a time period of interest in which the CPU is active and/or running tasks. For example, a duty cycle of 50% would indicate that the CPU is active (e.g., running one or more tasks) for half of the total time within a corresponding time period of interest (e.g., the CPU active time plus the CPU inactive/sleep time). The duty cycle of the CPU may be determined as an average duty cycle over a first period of time periodically over a longer second period of time. For example, an average duty cycle may be determined as an average of the duty cycles of each 30 minute period over a 23-hour period.

The term "foreground process" shall mean a process that is handled by a CPU in an interrupt context. Processes handled in the interrupt context may be performed on a prioritized basis, before completion of processes with a lower priority. Processes designated to be handled in the interrupt context include time-critical tasks and/or tasks that need to be completed with limited latency. Examples of foreground processes include processes implemented in connection with delivering therapy, communicating with other devices, analyzing signals, and the like.

The term "background process" shall mean a process that is handled outside of the interrupt context. Processes handled outside of the interrupt context may/may not be performed on a prioritized basis and/or may be performed when there are no remaining foreground processes waiting to be performed. Processes that are designated to be handled outside of the interrupt context include non-time critical tasks and/or tasks that do not need to be completed with limited latency. Examples of background processes include processes implemented in connection with monitoring signals, self-diagnostics, internal maintenance, and the like.

System Overview

Embodiments herein describe novel methods and systems to monitor and/or detect undesirable CPU activity patterns. The methods and systems may terminate and/or restart tasks and/or processes and/or provide alerts to users so that appropriate actions may be taken to manage the IMD based on detecting undesirable CPU activity patterns. The methods and systems herein provide tremendous value by monitoring CPU activity patterns as a generic but powerful complemental detection strategy to indirectly catch potential failures in firmware, hardware, or cyber security of IMDs.

Additionally, embodiments herein provide for methods and systems to monitor and/or detect undesirable CPU activity patterns (e.g., by monitoring duty cycle of the CPU) to provide early detection of rare and/or unexpected events. For example, early stages of lead fracture or insulation breach may not cause impedance changes that trigger generation of an alert. However, early stages of lead fracture or insulation breach may create low-level noises on the sensing channel. These low-level noises may activate the noise detection feature repeatedly, but without reaching the threshold required to trigger an actual noise response. In such cases, the present methods and systems enable detection of the duty cycle increase due to the repeated activation of the noise detection feature by the low-level noises, providing valuable early warning of the lead condition deterioration. In another example, a failure in firmware may repeatedly insert the same task into a task queue (e.g., based on a communication session prematurely ending due to a patient walking away from an external device during the communication session), creating a phantom task that does not interrupt other tasks but that does cause an undesirable increase in CPU activity patterns. In response to detecting increased CPU activity patterns, the present systems and methods provide for detection and termination of a phantom or repeated task. In another example, a hacker may repeatedly attempt to break into the IMD without success. Conventional cyber security controls implemented in the IMD may not raise a red flag since the attack attempts have all failed. However, such repeated hacking attempts may cause undesirable CPU activity patterns (e.g., abnormal duty cycle increases) due to attempts to wake-up/ping the IMD that are detectable by the present methods and systems. Additionally or alternatively, such repeated hacking attempts may cause the device to attempt to process communications that are detectable by the present methods and systems. In response to detecting undesirable CPU activity patterns, the methods and systems may detect the hacking attempts and provide a corresponding alert.

Embodiments herein also provide for innovative methods and systems for detecting undesirable changes in TH characteristics. Non-limiting examples of TH characteristics include TH time characteristics, duty cycle increases, and the like. In response thereto, the method and system may provide an alert to the user, terminate a task or process that is in progress, restart a task or process, re-boot all or a portion of the processes implemented by the device, and the like. For example, during product development, the developers may measure the various task handling time characteristics such as waiting time in queue, execution time, and execution frequency, as well as the overall CPU duty cycle. The results may be stored for the device to use as reference or baseline TH characteristics. During post-implantation IMD operation, the IMD may monitor the TH characteristics continuously, periodically, or responsive to certain criteria as the IMD encounters and/or responds to various types of events and provides related therapies. Types of events may include types of cardiac input, environmental events, communication tasks, or the like. The IMD determines that the CPU is experiencing an undesirable change in task handling upon determining that the TH characteristics deviate from the baseline TH characteristics by more than a predefined margin. In response thereto, the IMD may then generate an alert and send the alert to a local external device and/or a remote monitoring device or server for the care provider's attention. During a follow-up clinic session, the IMD may provide a detailed description of the TH characteristics regarding the change in task handling. Such information may be reviewed together with other diagnostic data (e.g., pacing events histograms, environmental events etc.) aid the care provider in identifying the potential issue in order to improve patient safety. Additionally or alternatively, in response to determining that a non-critical task is causing an undesirable and/or unacceptable increase in duty cycle, the methods and systems herein provide for a duty monitoring task manager that can terminate and/or reset the non-critical task.

Embodiments may be implemented in connection with one or more implantable medical devices (IMDs). Non-limiting examples of IMDs include one or more of neuro-stimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351, titled "Neurostimulation Method And System To Treat Apnea"; and U.S. Pat. No. 9,044,610, titled "System And Methods For Providing A Distributed Virtual Stimulation Cathode For Use With An Implantable Neurostimulation System", which are hereby incorporated by reference in their entireties. Additionally or alternatively, the IMD may include one or more structural and/or functional aspects of the device(s) described in U.S. Pat. No. 9,216,285, entitled "Leadless Implantable Medical Device Having Removable and Fixed Components"; and U.S. Pat. No. 8,831,747, entitled "Leadless Neurostimulation Device And Method Including The Same", which are hereby incorporated by reference in their entireties. Additionally or alternatively, the IMD may include one or more structural and/or functional aspects of the device(s) described in U.S. Pat. No. 8,391, 980, titled "Method And System For Identifying A Potential Lead Failure In An Implantable Medical Device"; and U.S. Pat. No. 9,232,485, titled "System And Method For Selectively Communicating With An Implantable Medical Device", which are hereby incorporated by reference in their entireties.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No.

15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties.

Additionally or alternatively, the IMD may be a leadless cardiac monitor (ICM) that includes one or more structural and/or functional aspects of the device(s) described in U.S. Patent Application, U.S. patent application Ser. No. 15/084, 373, filed Mar. 29, 2016, titled, "Method And System To Discriminate Rhythm Patterns In Cardiac Activity"; U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns", which are hereby incorporated by reference in their entireties.

Further, one or more combinations of IMDs may be utilized from the above incorporated patents and applications in accordance with embodiments herein.

FIG. 1 illustrates an IMD 100 and external device 104 coupled to a heart in a patient and implemented in accordance with embodiments herein. The external device 104 may be a programmer, an external defibrillator, a workstation, a portable computer, a personal digital assistant, a cell phone, a bedside monitor, or the like. The IMD 100 may represent a cardiac monitoring device, pacemaker, cardioverter, cardiac rhythm management device, defibrillator, neurostimulator, leadless monitoring device, leadless pacemaker or the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and then transmitted wirelessly to the external device 104. Hence, the external device 104 receives the IEGM cardiac signals through telemetry circuit inputs. The physician or another user controls operation of the external device 104 through a user interface.

Implantable Medical Device

Figure 2:
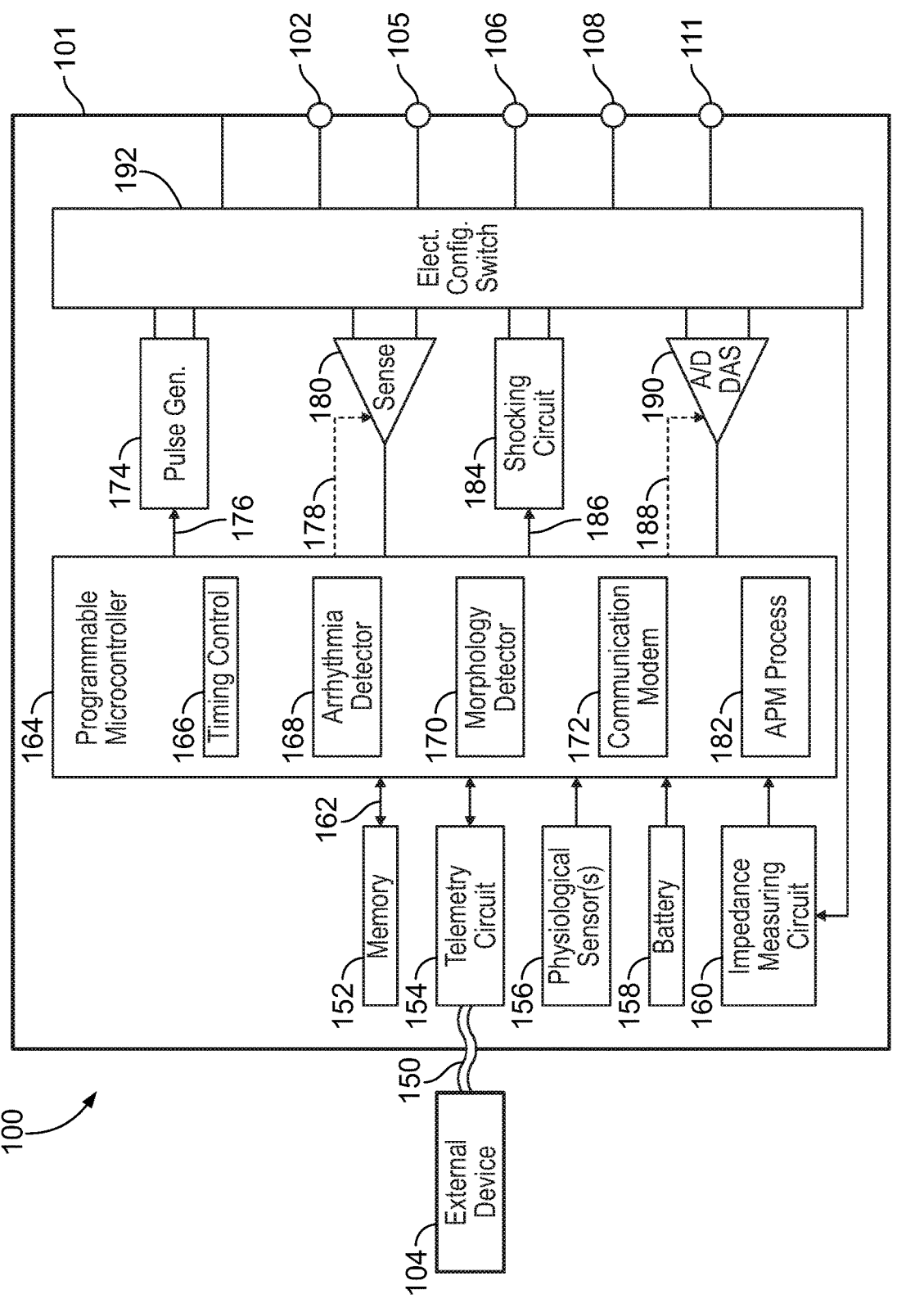
FIG. 2 illustrates a block diagram of the IMD of FIG. 1 in accordance with embodiments herein.

FIG. 2 illustrates a block diagram of the IMD 100 of FIG. 1 in accordance with embodiments herein. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a housing 101 to hold the electronic/computing components. The housing 101 (which is often referred to as the "can", "case", "encasing", or "case electrode") may be programmably selected to act as the return electrode for certain stimulus modes. The housing 101 further includes a connector (not shown) with a plurality of terminals 102, 105, 106, 108, and 111. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 111 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. Microcontroller 164 includes one or more microprocessors or CPUs (or equivalent control circuitry), RAM and/or ROM memory, logic and timing circuitry, state machine circuitry, and I/O circuitry.

The IMD 100 further includes a first chamber pulse generator 174 that generates stimulation pulses for delivery by one or more electrodes coupled thereto. The pulse generator 174 may deliver pacing pulses and/or anti-tachy pacing therapy. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164. In the example of FIG. 2, a single pulse generator 174 is illustrated. Optionally, the IMD 100 may include multiple pulse generators, similar to pulse generator 174, where each pulse generator is coupled to one or more electrodes and controlled by the microcontroller 164 to deliver select stimulus pulse(s) to the corresponding one or more electrodes.

The microcontroller 164 is illustrated to include timing control circuitry 166 to control the timing of the stimulation pulses (e.g., pacing rate, atrio-ventricular (AV) delay, atrial inter-conduction (A-A) delay, or ventricular inter-conduction (V-V) delay, etc.). The timing control circuitry 166 may also be used for the timing of refractory periods, blanking intervals, noise detection windows, evoked response windows, alert intervals, marker channel timing, and so on. Microcontroller 164 also has, an activation pattern management (APM) process 182 for monitoring CPU behavior, an arrhythmia detector 168 for detecting arrhythmia conditions, and a morphology detector 170 to review and analyze one or more features of the morphology of cardiac signals. The APM process 182 or any other process implemented on the microcontroller 164 may be implemented as firmware, software and/or circuits. Although not shown, the microcontroller 164 may further include other dedicated circuitry and/or firmware/software components that assist in monitoring various conditions of the patient's heart and managing pacing therapies.

The APM process 182 manages a processing activity pattern of the IMD 100. The APM process 182 may manage the processing activity pattern by monitoring CPU behavior to identify undesired changes in TH patterns. The APM process 182 stores one or more baseline TH patterns in a baseline TH pattern library. The APM process 182 monitors TH characteristics in connection with the one or more tasks based on the IMD performing one or more tasks (e.g., collecting the CA signals, analyzing the CA signals, delivering therapy, detecting communications requests, maintaining communication sessions with an external device, and the like). The APM process 182 may monitor the TH characteristics continuously or periodically or in response to certain criteria as the IMD 100 encounters and/or responds to various types of events (e.g., cardiac input, environmental events, communication tasks, etc.) and provides related therapies. The APM process 182 compares the TH characteristics to the baseline TH pattern. The APM process 182 determines that the CPU is experiencing an undesirable change in task handing based on determining that one or more TH characteristics deviate from the baseline TH pattern by more than a predetermined margin. The APM process 182 continues to monitor TH characteristics is connection with the IMD 100 performing one or more tasks based on the determining that the TH characteristics do not deviate from the baseline TH pattern by more than the predetermined margin.

In response to determining that the IMD 100 exhibits undesired changes in a TH pattern, the APM process 182 implements a corrective action. In one example, the APM process 182 may implement a corrective action by providing an alert to a user. For example, the APM process 182 may generate and transmit an alert to a local external device and/or a remote monitoring device or server, or may activate a patient notifier in special cases, for the user's attention. During a follow-up session (e.g., a clinical session, a diagnostics session, a communication session, or the like), the APM process 182 may provide a detailed description of the TH characteristics regarding the change in task handling. Such information may be reviewed together with other diagnostic data (e.g., pacing events histograms, environmental event logs, etc.) aid the care provider in identifying the potential issue in order to improve patient safety. Additionally or alternatively, the APM process may implement a corrective action by terminating a task or process that is in progress. Additionally or alternatively, the APM process may implement a corrective action by restarting a task or process in progress one or more times before full termination of the task or process. For example, in response to determining that a non-critical task is causing an undesirable and/or unacceptable increase in duty cycle, the APM process 182 may terminate the non-critical task.

The IMD 100 is further equipped with a communication modem (modulator/demodulator) 172 to enable wireless communication with other devices, implanted devices and/ or external devices. In one implementation, the communication modem 172 may use high frequency modulation of a signal transmitted between a pair of electrodes. In one implementation, the communication modem 172 uses high frequency modulation, for example using RF (e.g., MICS band or the like), Bluetooth, or Bluetooth Low Energy telemetry protocols. The signals are transmitted in a high frequency range and will travel through the body tissue in fluids without stimulating the heart or being felt by the patient. The communication modem 172 may be implemented in hardware as part of the microcontroller 164, or as software/firmware instructions programmed into and executed by the microcontroller 164. Alternatively, the communication modem 172 may reside separately from the microcontroller as a standalone component. The communication modem 172 facilitates data retrieval from a remote monitoring network. The communication modem 172 enables timely and accurate data transfer directly from the patient to an electronic device utilized by a physician.

The IMD 100 includes sensing circuitry 180 selectively coupled to one or more electrodes that perform sensing operations, through the switch 192 to detect the presence of cardiac activity in the right chambers of the heart. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuits, similar to sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or in a bipolar sensing configuration.

The IMD 100 further includes an analog-to-digital (A/D) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. Furthermore, baseline TH patterns are stored in memory 152 in a baseline TH pattern library and are used in the APM process in determining whether the IMD 100 exhibits undesired changes in TH patterns.

The operating parameters of the IMD 100 may be non-invasively programmed into the memory 152 through a telemetry circuit 154 in telemetric communication via communication link 150 with the external device 104. The telemetry circuit 154 allows intracardiac electrograms and status information relating to the operation of the IMD 100 (as contained in the microcontroller 164 or memory 152) to be sent to the external device 104 through the established communication link 150.

The IMD 100 may further include magnet detection circuitry (not shown), coupled to the microcontroller 164, to detect when a magnet is placed over the unit. A magnet may be used by a clinician to perform various test functions of the unit 100 and/or to signal the microcontroller 164 that the external programmer is in place to receive or transmit data to the microcontroller 164 through the telemetry circuits 154.

The IMD 100 may further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. The microcontroller 164 responds by adjusting the various pacing parameters (such as rate, AV Delay, V-V Delay, etc.) at which the atrial and ventricular pacing pulses are administered. While shown as being included within the unit 100, the physiologic sensor(s) 156 may be external to the unit 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the unit 100 employs lithium/silver vanadium oxide batteries.

Optionally, the IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used. Optionally, the microcontroller 164 further controls a shocking circuit 184 by way of a control signal 186. The shocking circuit 184 generates shocking pulses of low (e.g., up to 0.5 joules), moderate (e.g., 0.5-10 joules), or high energy (e.g., 111 to 40 joules), as controlled by the microcontroller 164.

The IMD 100 may be operated as an implantable cardioverter defibrillator (ICD) device, which detects the occurrence of an arrhythmia and automatically applies an appropriate electrical shock therapy to the heart aimed at terminating the detected arrhythmia. To this end, the microcontroller 164 further controls a shocking circuit 184 by way of a control signal 186. The shocking circuit 180 generates shocking pulses of low (e.g., up to 0.5 joules), moderate (e.g., 0.5-10 joules), or high energy (e.g., 11 to 40 joules), as controlled by the microcontroller 164. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD 100.

Management of CPU Activation Patterns

Figure 3:
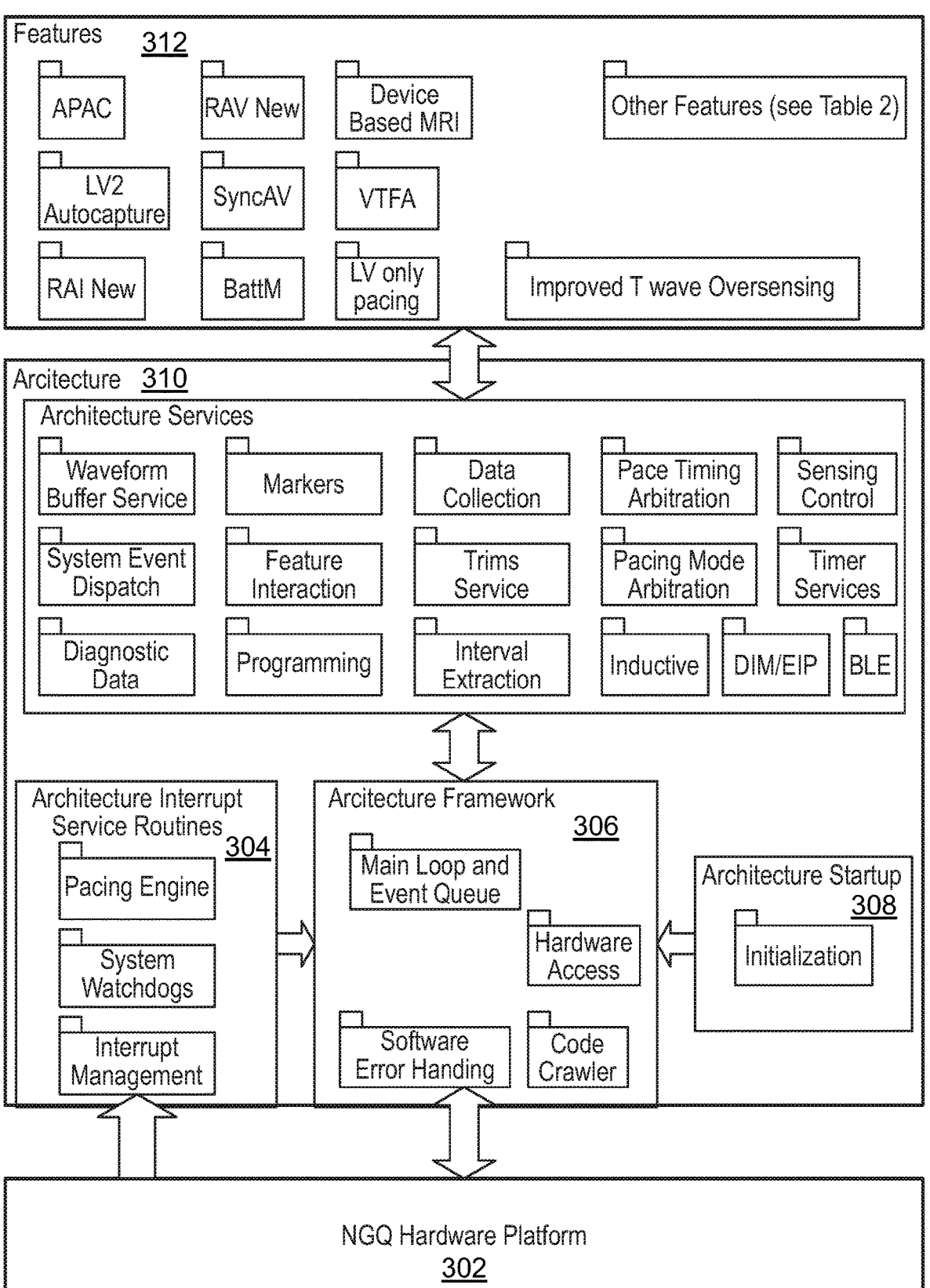
FIG. 3 illustrates an architecture block diagram of examples of various features, services, and frameworks that may be implemented by an IMD hardware platform in accordance with embodiments herein.

FIG. 3 illustrates an architecture block diagram of examples of various features, services and frameworks that may be implemented by an IMD hardware platform in accordance with embodiments herein. For example, the various features, services, and frameworks may be implemented on one or more microcontrollers 164 of the IMD 100 in connection with the APM process 182 and other IMD functions. The IMD hardware platform 302 may evoke operation of an interrupt handler 304 implemented as part of the embedded device software 306 based on detecting a triggering event (e.g., detecting noise on a sensing channel, attempts to communicate with the IMD 100, etc.). The interrupt handler 304 may include one or more service routines corresponding to one or more of a pacing engine, system watchdogs, interrupt management, or the like. The interrupt handler 304 may detect and facilitate performing any critical tasks (e.g., pacing) in the interrupt context. The IMD hardware platform 302 may also evoke operation of the architecture framework 306. The architecture framework 306 may include one or more service routines corresponding to one or more of software error handling, code crawlers, hardware access, main loop and/or event queues, or the like. The architecture framework 306 may call on one or more start-up routines of the architecture startup 308 (e.g., an initialization routine). The architecture framework 306 may also call on one or more architecture services 310 in performing tasks. The architecture services 310 may include one or more services corresponding to one or more of waveform buffer services, markers, data collection, system event dispatch, diagnostic data, feature interaction, programming, trims services, interval extraction, pace timing arbitration, pacing mode arbitration, inductive services, sensing control, timer services, DIM/EIP, BLE, or the like. In turn, the architecture services 310 may evoke one or more features 312 the IMD 100 in connection with the APM process 182 and/or other IMD functions. Examples of features 312 may include one or more of primary sensing algorithms, secondary confirmation algorithms, therapy algorithms, diagnostic algorithms, maintenance algorithms, communications algorithms, or the like.

FIG. 4 illustrates a characterization process for determining and storing TH characteristics in accordance with embodiments herein. All or a portion of the operations of FIG. 4 may be implemented by one or more processors of the IMD 100 configured with executable instructions. Portions of the operations of FIG. 4 may also be implemented by one or more processors of one or more of a local external device and/or a remote server. Although the operations of FIG. 4 are described in at least a partially serial manner, it is recognized that at least a portion of the operations are performed in parallel. Furthermore, the operations of FIG. 4 may be performed in parallel with other operations of the IMD 100.

At 402, the one or more processors of the IMD 100 determine the times to complete one or more tasks in a queue. The times to complete a given task may include TH characteristics such as a wait time in which a task remains in the queue and/or an execution time of a critical task (e.g., pacing). Examples of times to complete tasks may include one or more of i) the time to complete a type of sense event analysis (e.g., Brady R) after an interrupt is received; iii) a time to prepare and deliver a therapy (e.g., a V pulse); iv) a time to perform a measurement (e.g., an impedance measurement, a battery charge measurement); v) a time to collect and update a diagnostic based on the CA signals; vi) a time to complete a housekeeping task (e.g., a clean-up task at the end of a communication session); viii) a time to analyze an incoming data packet; ix) a time to transmit an outgoing data packet; or the like. The time to complete a given task may include the overhead based on multiple tasks being executed. Flow moves to 404 based on determining the times to complete the one or more tasks in the queue.

At 404, the one or more processors of the IMD 100 record the times to complete one or more tasks. The one or more TH characteristics associated with a given task may be recorded and used to build a histogram. For example, the process may build and/or maintain a histogram of the wait time and/or a histogram of the execution time associated with a task or a group of tasks. The histograms of distribution of the wait times and execution times for tasks may be measured on a periodic basis (e.g., daily or weekly) and measured values included in the corresponding histogram. Histograms of wait times and/or execution times may be used to compare currently measured wait times and/or execution times for one or more tasks against corresponding trends and/or patterns for wait times and/or execution times for the one or more tasks. The operations of 402 and 404 may be performed iteratively until no more tasks remain the queue. Flow moves to 406 based on recording the times to complete one or more tasks.

At 406, the one or more processors of the IMD 100 determine CPU activity during a sleep mode of the IMD 100. The IMD 100 enters the sleep mode based on there being no tasks in the queue. The process may insert a sleep response task in the queue to monitor CPU activity during the sleep mode of the IMD 100. For example, the process may monitor, as CPU activity during the sleep mode, a wake-to-sleep time. The wake-to-sleep time may be the difference between the time the queue reached an empty state and the time the CPU entered the sleep mode. Additionally or alternatively, the process may monitor the duration of time between the time the CPU entered the sleep mode and the time an interrupt terminated the sleep mode. Flow moves to 408 based on determining CPU activity during the sleep mode and the one or more processors of the IMD 100 record the CPU activity during the sleep mode of the IMD 100.

At 410, the one or more processors of the IMD 100 store the TH characteristics of each task as baseline TH patterns in a reference matrix.

FIG. 5 illustrates a process for managing a processing activity pattern of an IMD in accordance with embodiments herein. The managing includes monitoring CPU behavior to identify undesired changes in TH patterns. All or a portion of the operations of FIG. 5 may be implemented by one or more processors of the IMD 100 configured with executable instructions. Portions of the operations of FIG. 5 may also be implemented by one or more processors of one or more of a local external device and/or a remote server. Although the operations of FIG. 5 are described in at least a partially serial manner, it is recognized that at least a portion of the operations are performed in parallel. Furthermore, the operations of FIG. 5 may be performed in parallel with other operations of the IMD 100.

At 502, the one or more processors of the IMD 100 store a baseline TH pattern. In one non-limiting example, during product development, developers may measure the various TH time characteristics (e.g., waiting time in queue, execution time, execution frequency, overall and/or average CPU duty cycle, and the like). The results of the measurements of the various TH time characteristics may be stored as one or more TH baseline patterns in the TH baseline pattern library. Additionally or alternatively, one or more TH baseline patterns may be identified as part of the monitoring operation at 506 and the one or more TH baseline patterns may be periodically stored in the TH baseline pattern library. Additionally or alternatively, the TH baseline patterns may be updated periodically or on demand. For example, the TH baseline patterns may be updated based on changing one or more programming parameters of the IMD that may impact the TH time characteristics. Flow moves to 504 upon storing the baseline TH pattern.

At 504, the one or more processors of the IMD perform tasks associated with one or more of collecting CA signals and/or environmental event signals, analyzing CA signals and/or environmental event signals, delivering therapy, detecting communications requests, maintaining communications sessions with an external device. The tasks may include time-critical tasks implemented in connection with foreground processes (e.g., delivering therapy, communicating with external devices, analyzing signals, etc.). Additionally, the tasks may include non-time-critical tasks associated with background processes (e.g., self-diagnostics, internal maintenance, monitoring signals, etc.). Flow moves to 506 based on performing the tasks.

At 506, the one or more processors of the IMD 100 monitor a TH characteristic in connection with the performing the tasks. The TH characteristic may represent at least one of a CPU TH time characteristic (e.g., times for the CPU to perform types of tasks), a CPU continuous active duration, a CPU continuous sleep duration, a duty cycle measurement for a select period of time, a queue waiting time for a task, an execution time for a critical task (e.g., pacing), a queue waiting time for a group of tasks, or an execution time for a group of tasks. The CPU continuous active duration may represent a duration of time where the CPU is continuously active and performing tasks in a queue. The CPU continuous sleep duration may represent a duration of time where the CPU is continuously inactive/in a sleep mode and does not perform any tasks. The TH characteristic may represent at least one of i) time to complete a type of sense event analysis; ii) time to complete a type of external input processing; iii) a time to prepare and deliver a therapy (e.g., a V pulse); iv) a time to perform a measurement (e.g., an impedance measurement, a battery charge measurement); v) a time to collect and update a diagnostic based on the CA signals; vi) a time to complete a housekeeping task; viii) a time to analyze an incoming data packet; ix) a time to transmit an outgoing data packet; and the like. For example, the time to complete a type of sense event analysis (e.g., Brady R) may be measured. In another example, the time to complete a type of external input processing (e.g., related to a magnet, an activity, etc.) is measured after an input is received. Additionally or alternatively, the monitoring may be temporarily suspended during a clinical session, a communication session with a remote monitoring device and/or a server, or the like (e.g., to prevent monitoring and/or recording TH characteristics that are not due to normal IMD 100 operation).

Additionally or alternatively, monitoring the TH characteristic may include identifying, as part of the TH characteristic, a duty cycle of a CPU. For example, a duty cycle of a CPU may be the percentage of time that the CPU is active and running tasks over the total time period of interest. Further additionally or alternatively, the duty cycle of the CPU may be determined as an average duty cycle over a first period of time periodically over a longer second period of time. For example, an average duty cycle may be determined as an average of the duty cycles of each 30 minute period over a 23-hour period.

Additionally or alternatively, monitoring the TH characteristic may include maintaining at least one of a histogram of a wait time in which a task remains in a queue or a histogram of an execution time for select critical tasks. Flow moves to 508 based on monitoring the TH characteristic.

Additionally or alternatively, monitoring the TH characteristic may include maintaining at least one of a histogram of a wait time in which a task remains in a queue or a histogram of an execution time for tasks (e.g., all tasks or select critical tasks). The histograms of distribution of the wait times and execution times for tasks may be measured on a periodic basis (e.g., daily or weekly) and measured values included in the corresponding histogram. Maintaining histograms of wait times and/or execution times of tasks may be used post-implantation to establish and update the baseline TH patterns in the baseline TH pattern library continuously, periodically, or in response to certain conditions of the IMD 100.

At 508, the one or more processors of the IMD 100 compare the TH characteristic to the baseline TH pattern. Comparing one or more TH characteristics to corresponding baseline TH patterns may facilitate the detection of potential failures in firmware, hardware, or cybersecurity of the IMD 100. Comparing the TH characteristic to the baseline TH pattern includes determining whether the TH characteristic has deviated from the baseline TH pattern by more than a predetermined margin. TH characteristics may deviate from baseline TH patterns based on events such as, for example and without limitation, low-level impedance changes on the sensing channel resulting from early stages of lead fracture and/or insulation breach, a failure in firmware (e.g., due to prematurely ending a communication session of the IMD 100) that creates a phantom task (e.g., a task that is erroneously and repeatedly inserted into the queue) that does not otherwise interrupt other tasks, repeated and/or unsuccessful attempts by a hacker to wake-up/ping and/or communicate with the IMD 100, or the like. The process interprets the processing activity pattern of the IMD (e.g., the CPU behavior) to exhibit undesired changes in TH patterns based on the compare indicating that the TH characteristic does deviate from the baseline TH pattern by more than the predetermined margin, and the flow moves to 510. Alternatively, the process interprets the processing activity pattern of the IMD (e.g., the CPU behavior) does not exhibit undesired changes in TH patterns based on the compare indicating that the TH characteristic does not deviate from the baseline TH pattern by more than the predetermined margin, and the flow returns to 504.

In one example, the CPU TH time characteristics to one or more baseline TH patterns in a baseline TH pattern library. The one or more baseline TH patterns may be based, at least in part, on the various TH time characteristics measured by the developers and stored in memory prior to implantation of the IMD 100. Additionally or alternatively, the one or more baseline TH patterns may be based, at least in part, on moving averages or trends of a wait time in which a task remains in a queue and/or an execution time for select critical tasks. Moving averages and/or trends of the wait time in which a task remains in a queue and/or the execution time for select critical tasks may be based, at least in part, on corresponding histograms maintained during the monitoring at operation 506. Additionally or alternatively, moving averages and/or trends of the wait time in which a task remains in a queue and/or the execution time for select critical tasks may be periodically stored as baseline task handling patterns at operation 502.

Additionally or alternatively, based on a duty cycle of the CPU identified as part of the TH characteristic, the compare includes determining whether the duty cycle of the CPU indicates that the CPU is continuously active for at least a predetermined amount of time. A baseline TH pattern for the duty cycle of the CPU may be identified as a duration threshold (e.g., 3 hours) or percent of run time or sleep time (e.g., 25%) of the CPU over a select time period (e.g., a day or week). Optionally, the baseline TH pattern for the duty cycle of the CPU may be further identified as a predetermined number of times the duration threshold is reached (e.g., 3 times) during the select time period. In the case of monitoring CPU continuous active duration (e.g., without sleep), the baseline TH pattern for the duty cycle may be selected to prevent a risk of CPU overrun.

Additionally or alternatively, based on the duty cycle representing an average duty cycle over a first period of time periodically over a longer second period of time, the compare includes determining whether the duty cycle of the CPU exceeds the baseline TH pattern. Many tasks implemented on an IMD 100 are correlated to cardiac events which are periodic in nature (e.g., occurring every 1 s interval) and monitoring a daily average of a duty cycle may simply aspects of the methods and systems described herein. A baseline TH pattern for an average duty cycle over a first period of time periodically over a longer second period of time may be a daily average (e.g., over every 24-hour period) of the of the duty cycle (e.g., 30 minutes) for a consecutive number (e.g., 3) of 24 hour periods.

At 510, the one or more processors of the IMD 100 implement a corrective action in response to the compare of the TH characteristic and the baseline TH pattern. The corrective action may be implemented in response to the compare indicating that the TH characteristic has deviated from the baseline TH pattern by more than a predetermined margin. The TH characteristic deviating from the baseline pattern by more than the predetermined margin indicates that the processing activity pattern of the IMD (e.g., the CPU behavior) is exhibiting undesired changes in TH patterns. As part of implementing a corrective action, the one or more processors of the IMD 100 may provide an alert to the user, terminate a task or process that is in progress, restart a task or process, re-boot all or a portion of the processes implemented in the IMD 100, or the like. For example, the process may implement a corrective action by generating and transmitting an alert to a local external device and/or a remote monitoring device or server, or may activate a patient notifier, for the user's attention. During a follow-up session (e.g., a clinical session, a diagnostics session, a communication session, or the like), the APM process 182 may provide a detailed description of the TH characteristics regarding the change in task handling. Such information may be reviewed together with other diagnostic data (e.g., pacing events histograms, environmental event logs, etc.) aid the care provider in identifying the potential issue (e.g., early stages of lead fracture or insulation breach) in order to improve patient safety. In an additional or alternative example, the process may implement a corrective action by terminating a task or process that is in progress (e.g., a task being repeatedly inserted by the firmware resulting from a communication session prematurely ending, a task related to a communication attempt of a hacker that breaches a physical communication layer, or the like). For example, in response to determining that a non-critical task is causing an undesirable and/or unacceptable increase in duty cycle, the APM process 182 may terminate the non-critical task, and, optionally, restart the non-critical task one or more times before terminating the non-critical task.

Figure 6:
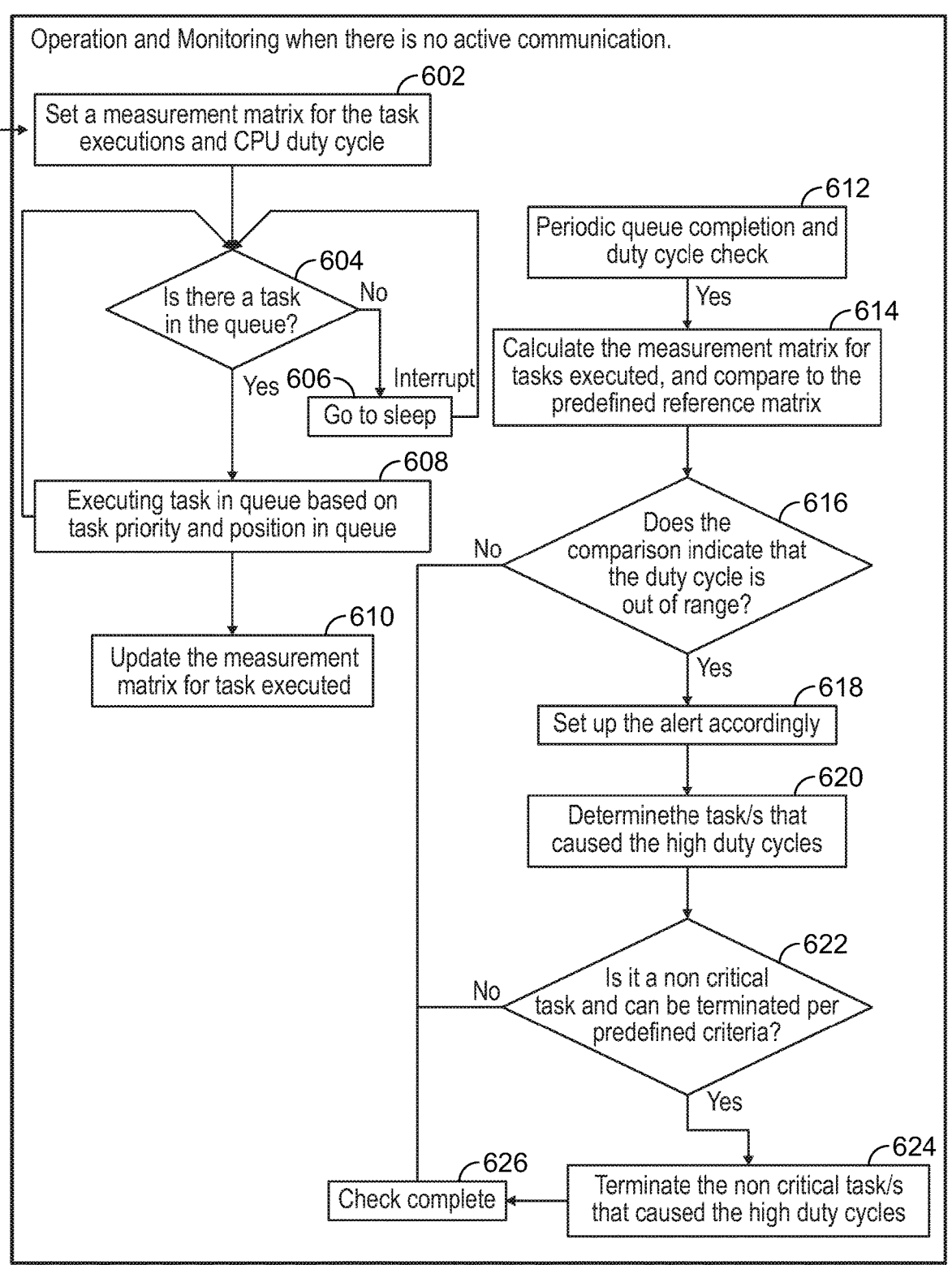
FIG. 6 illustrates one example of a process for monitoring CPU behavior to identify undesired changes in TH patterns in accordance with embodiments herein.

FIG. 6 illustrates one example of a process for monitoring CPU behavior to identify undesired changes in TH patterns in accordance with the processes of FIGS. 4 and 5. All or a portion of the operations of FIG. 6 may be implemented by one or more processors of the IMD 100 configured with executable instructions. Portions of the operations of FIG. 6 may also be implemented by one or more processors of one or more of a local external device and/or a remote server. Although the operations of FIG. 6 are described in at least a partially serial manner, it is recognized that at least a portion of the operations are performed in parallel. Furthermore, the operations of FIG. 6 may be performed in parallel with other operations of the IMD 100.

At 602 the one or more processors of the IMD 100 set a measurement matrix for the task executions and the CPU duty cycle. The measurement matrix may be based, at least in part, on the reference matrix stored at operation 410 of FIG. 4 and in accordance with operation 502 of FIG. 5. Flow moves to 604 based on setting a measurement matrix. At 604, the one or more processors of the IMD 100 determine if there is a task in the queue. Flow moves to 606 based on determining there is no task in the queue and the one or more processors of the IMD 100 enter a sleep state of the IMD. The one or more processors of the IMD 100 may periodically execute an interrupt and determine whether there are any tasks in the queue during the sleep state. Returning to 604, based on determining that there are one or more tasks in the queue, flow moves to 608. At 608, the one or more processors of the IMD 100 perform the one or more tasks based on the task positions in the queue and priorities assigned to the tasks according to operation 504 of FIG. 5. Flow moves to 608 based on executing the one or more tasks. At 608, the one or more processors of the IMD 100 update the measurement matrix associated with the one or more tasks. Updating the measurement matrix may include monitoring one or more TH characteristics in connection with performing the tasks according to operation 506 of FIG. 5. Flow returns to 604 and the one or more processors of the IMD 100 determine whether there is a task in the queue based on updating the measurement matrix.

Separately, and on a periodic basis, the one or more processors of the IMD 100 perform operations to monitor the CPU behavior to identify undesired changes in TH patterns on a periodic basis (e.g., daily, hourly, etc.). Additionally or alternatively, the operations to monitor the CPU behavior may be performed on an interrupt basis. At 612, the one or more processors of the IMD 100 initiate monitoring the CPU behavior and flow moves to 614. At 614, the one or more processors of the IMD 100 determine the measurement matrix for the tasks executed and compare the measurement matrix (e.g., the current measurement matrix as stored at operation 610) to the baseline measurement matrix. At 616, the one or more processors of the IMD 100 compare the current measurement matrix to the reference matrix stored at operation 410 of FIG. 4 to determine whether one or more TH characteristics deviate from corresponding baseline TH patterns by more than the predetermined margin in accordance with operation 508 of FIG. 5. Flow moves to 626 and the process ends based on determining that no TH characteristics deviate from the corresponding baseline TH patterns by more than the predetermined margin. Flow moves to 618 based on determining that one or more TH characteristics do deviate from the corresponding baseline TH patterns by more than the predetermined margin. At 618, the one or more processors of the IMD 100 generate an alert. Flow moves to 620 upon generating an alert.

At 620, the one or more processors of the IMD 100 determine the one or more tasks that caused the undesired changes in the TH patterns. For example, the process may determine the one or more tasks to relate to repeated activation of a noise detection feature that falls below a threshold to trigger a noise response. Repeated activation of the noise detection feature below the noise response threshold may be used, alone or in conjunction with other diagnostic data, to indicate the early stages of lead fracture or insulation breach. In another example, the process may determine the one or more tasks to be tasks that are being repeatedly inserted into the queue by the firmware and to correspond to clean up tasks implemented based on a patient prematurely ending a communication session of the IMD 100 (e.g., by walking away from an external device). In another example, the process may determine that the one or more tasks relate to repeated attempts to wake up/ping the IMD 100 that are different than the periodic interrupts resulting from cardiac events or relate to communications that breach a physical communication layer but that never actually control the IMD 100. Repeated attempts to wake up/ping the IMD 100 and/or communications that breach only the outer communications layers may indicate a hacking attempt and/or a cybersecurity breach. The process may generate and transmit an alert and/or report to a local external device and/or a remote monitoring device or server regarding the repeated activation of the noise detection feature, the repeated attempts to ping/wake up the IMD 100, the unsuccessful communications, or the repeated insertion of tasks into the queue by the firmware. Flow moves to 622 based on determining the one or more tasks that caused the undesired changes in the TH patterns.

At 622, the one or more processors of the IMD 100 determine whether the one or more tasks that caused the undesired changes in the TH patterns are non-critical tasks that can be terminated per predefined criteria. For example, the process determines tasks that relate to foreground processes (e.g., delivering therapy, communicating with external devices, analyzing signals, and the like) to be critical tasks that cannot be terminated per the predefined criteria. The process ends at 626 based on determining the tasks cannot be terminated. Additionally or alternatively, the process determines tasks that relate to background processes (e.g., monitoring signals, self-diagnostics, internal maintenance, and the like) to be non-critical tasks that can be terminated per the predefined criteria. Flow moves to 624 based on determining that the one or more tasks are non-critical task that can be terminated. At 624, the one or more processors of the IMD 100 terminate the one or more non-critical tasks and the process ends at 626. The process may terminate the one or more non-critical tasks by one or more of resetting a feature and/or a process associated with the one or more tasks (e.g., restarting a communications chip or process), cleaning out the queue, re-booting the IMD 100, or the like. For example, the process may implement a duty monitoring task manager that can terminate the one or more non-critical tasks. Optionally, the process may restart the one or more non-critical tasks one or more times before terminating the non-critical tasks. Additionally or alternatively, the process may implement a scheme to mask repeated attempts to ping/wake up the IMD 100 (e.g., by masking communications attempts during times when communications attempts are not expected, by unmasking interrupts only every 1-2 minutes to check for valid communications, or the like). Operations 618-626 may be performed in accordance with operation 510 of FIG. 5.

Accordingly, the methods and systems described herein enable monitoring and detection of undesirable changes in TH characteristics, thereby facilitating identification and mitigation of potential malfunctions and/or failures in firmware, hardware, or cybersecurity. Additionally or alternatively, based on detecting that a non-critical task is causing an undesirable increase in a TH characteristic, the methods and systems described herein may mange (e.g., terminate, re-boot, etc.) the non-critical task, thereby preserving battery life.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-transitory computer (device) readable medium(s) may be utilized. The non-transitory medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. An implantable medical device (IMD), comprising:
memory to store a baseline task handling (TH) pattern for CPU behavior of one or more processors over time; and
TH circuitry including the one or more processors, the TH circuitry configured to:
perform one or more tasks associated with one or more of collecting one or more cardiac activity (CA)

signals or environmental event signals, analyzing the one or more CA signals or environmental event signals, delivering therapy, detecting communications requests, or maintaining communications sessions with an external device;

monitor a TH characteristic, indicative of at least one of a CPU processing activity pattern or a CPU task execution time, in connection with the performing the one or more tasks;

compare the TH characteristic to the baseline TH pattern; and implement a corrective action in response to the compare operation of the TH characteristic and the baseline TH pattern.

2. The IMD of claim 1, wherein the corrective action is implemented in response to the compare operation indicating that the TH characteristic has deviated from the baseline TH pattern by more than a predetermined margin.

3. The IMD of claim 1, wherein at least one of:
i) the TH characteristic, indicative of the CPU processing activity pattern, represents at least one of a CPU TH time characteristic, a CPU continuous active duration, a CPU continuous sleep duration, a CPU duty cycle for a select period of time, or
ii) the TH characteristic, indicative of the CPU task execution time, represents at least one of a queue waiting time for a task, an execution time for a critical task, a queue waiting time for a group of tasks, or an execution time for a group of tasks.

4. The IMD of claim 3, wherein the TH characteristic represents the CPU TH time characteristic for at least one of:
i) time to complete a type of sense event analysis;
ii) time to complete a type of external input processing;
iii) a time to transmit an outgoing data packet;
iv) a time to perform a measurement;
v) a time to collect and update a diagnostic based on the CA signals;
vi) a time to complete a housekeeping task; and
vii) a time to analyze an incoming data packet.

5. The IMD of claim 1, wherein the monitor operation includes identifying, as the TH characteristic indicative of the CPU processing activity pattern, a duty cycle of a CPU and the compare operation includes determining whether the duty cycle of the CPU indicates that the CPU is continuously active for at least a predetermined amount of time.

6. The IMD of claim 5, wherein the duty cycle of the CPU is determined as an average duty cycle over a first period of time periodically over a longer second period of time.

7. The IMD of claim 1, wherein the TH characteristic is indicative of the CPU task execution time and wherein the monitor operation includes maintaining at least one of a histogram of a wait time in which a task remains in a queue or a histogram of an execution time for select critical tasks, the corrective action implemented based on the histogram.

8. The IMD of claim 1, wherein the implement operation includes at least one of terminating a task or process that is in progress, restart a task or process, or re-boot a portion or all of the processes implemented by the IMD.

9. A method of managing a CPU behavior of an implantable medical device (IMD), the method comprising:
storing a baseline task handling (TH) pattern for the CPU behavior of one or more processors over time;
performing one or more tasks associated with one or more of collecting one or more cardiac activity (CA) signals or environmental event signals, analyzing the one or more CA signals or environmental event signals, delivering therapy, detecting communications requests, maintaining communications sessions with an external device;

monitoring a TH characteristic, indicative of at least one of a CPU processing activity pattern or a CPU task execution time, in connection with the performing the one or more tasks;

comparing the TH characteristic to the baseline TH pattern; and implementing a corrective action in response to the compare operation of the TH characteristic and the baseline TH pattern.

10. The method of claim 9, wherein the corrective action is implemented in response to the compare operation indicating that the TH characteristic has deviated from the baseline TH pattern by more than a predetermined margin.

11. The method of claim 9, wherein at least one of:
i) the TH characteristic, indicative of the CPU processing activity pattern, represents at least one of a CPU TH time characteristic, a CPU continuous active duration, a CPU continuous sleep duration, a CPU duty cycle for a select period of time, or
ii) the TH characteristic, indicative of the CPU task execution time, represents at least one of a queue waiting time for a task, an execution time for a critical task, a queue waiting time for a group of tasks, or an execution time for a group of tasks.

12. The method of claim 11, wherein the TH characteristic represents the CPU TH time characteristic for at least one of:
i) time to complete a type of sense event analysis;
ii) time to complete a type of external input processing;
iii) a time to transmit an outgoing data packet;
iv) a time to perform a measurement;
v) a time to collect and update a diagnostic based on the CA signals;
vi) a time to complete a housekeeping task; and
vii) a time to analyze an incoming data packet.

13. The method of claim 9, wherein the monitor operation includes identifying, as the TH characteristic indicative of the CPU processing activity pattern, a duty cycle of a CPU and the compare operation includes determining whether the duty cycle of the CPU indicates that the CPU is continuously active for at least a predetermined amount of time.

14. The method of claim 13, wherein the duty cycle of the CPU is determined as an average duty cycle over a first period of time periodically over a longer second period of time.

15. The method of claim 9, wherein the TH characteristic is indicative of the CPU task execution time and wherein the monitor operation includes maintaining at least one of a histogram of a wait time in which a task remains in a queue or a histogram of an execution time for select critical tasks, the corrective action implemented based on the histogram.

16. The method of claim 9, wherein the implement operation includes at least one of terminating a task or process that is in progress, restart a task or process, or re-boot a portion or all of the processes implemented by the IMD.

17. A computer program product comprising a non-transitory computer readable storage medium comprising computer executable code to:
perform one or more tasks associated with one or more of collecting cardiac activity (CA) signals, analyzing CA signals, delivering therapy, detecting communications requests, maintaining communications sessions with an external device;

monitor a TH characteristic, indicative of at least one of a CPU processing activity pattern or a CPU task execution time, in connection with the performing the one or more tasks;

compare the TH characteristic to a baseline TH pattern for CPU behavior of one or more processors over time; and implement a corrective action in response to the compare operation of the TH characteristic and the baseline TH pattern.

18. The computer program product of claim 17, wherein the corrective action is implemented in response to the compare operation indicating that the TH characteristic has deviated from the baseline TH pattern by more than a predetermined margin.

19. The computer program product of claim 17, wherein at least one of:

i) the TH characteristic, indicative of the CPU processing activity pattern, represents at least one of a CPU task handling time characteristic, a CPU continuous active duration, a CPU continuous sleep duration, a CPU duty cycle for a select period of time, or ii) the TH characteristic, indicative of the CPU task execution time, represents at least one of a queue waiting time for a task, an execution time for a critical task, a queue waiting time for a group of tasks, or an execution time for a group of tasks.

20. The computer program product of claim 17, wherein the TH characteristic represents the CPU TH time characteristic for at least one of:

i) time to complete a type of sense event analysis;

ii) time to complete a type of external input processing;

iii) a time to transmit an outgoing data packet;

iv) a time to perform a measurement;

v) a time to collect and update a diagnostic based on the CA signals;

vi) a time to complete a housekeeping task; and vii) a time to analyze an incoming data packet.

\* \* \* \* \*